US012171981B2

(12) United States Patent
Haslbeck (10) Patent No.: US 12,171,981 B2
(45) Date of Patent: Dec. 24, 2024

(54) MEDICAL PUMP DEVICE FOR CONVEYING A MEDICAL FLUID

(71) Applicant: B. Braun Melsungen AG, Melsungen (DE)

(72) Inventor: Karsten Haslbeck, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 709 days.

(21) Appl. No.: 17/422,796

(22) PCT Filed: Jan. 7, 2020

(86) PCT No.: PCT/EP2020/050218
§ 371 (c)(1),
(2) Date: Jul. 14, 2021

(87) PCT Pub. No.: WO2020/148115
PCT Pub. Date: Jul. 23, 2020

(65) Prior Publication Data
US 2022/0126018 A1 Apr. 28, 2022

(30) Foreign Application Priority Data

Jan. 15, 2019 (DE) ...................... 10 2019 200 399.0

(51) Int. Cl.
*A61M 5/152* (2006.01)
*A61M 5/14* (2006.01)
*A61M 5/168* (2006.01)

(52) U.S. Cl.
CPC ............ *A61M 5/152* (2013.01); *A61M 5/141* (2013.01); *A61M 5/16813* (2013.01); *A61M 5/16877* (2013.01); *A61M 2205/0216* (2013.01)

(58) Field of Classification Search
CPC ...... A61M 2205/0216; A61M 2206/12; A61M 2206/16; A61M 5/14; A61M 5/141;
(Continued)

(56) References Cited

U.S. PATENT DOCUMENTS

| 3,841,354 A | 10/1974 | Mcdonnell |
| 4,176,683 A | 12/1979 | Leibinsohn |

(Continued)

FOREIGN PATENT DOCUMENTS

| CN | 101437558 A | 5/2009 |
| CN | 102481407 A | 5/2012 |

(Continued)

OTHER PUBLICATIONS

Office Action received in Chinese Application No. 202080009423.3 dated Feb. 1, 2023, with translation, 9 pages.

(Continued)

*Primary Examiner* — Shefali D Patel
(74) *Attorney, Agent, or Firm* — Christopher A. Rothe; CM Law (57) ABSTRACT

A pump device for conveying a medical fluid, the pump device includes a membrane forming a pump volume. The membrane is expanded in a filling state of the pump volume with the medical fluid. The expanded membrane exerts a delivery pressure on the pump volume to deliver the medical fluid into a fluid-line system. The pump device also has a throttle device with a channel having an inlet connected to the pump volume and an outlet connectable to the fluid-line system. The delivery of the medical fluid through the outlet is finely adjustable to a flow rate at a time of manufacture. The throttle device has two bodies. The channel is formed between oppositely arranged surfaces of the bodies. The oppositely arranged surfaces are movable relative to each other for the fine adjustment of the flow rate during the (Continued)

manufacture, so that an effective length of the channel is variable.

8 Claims, 4 Drawing Sheets

(58) Field of Classification Search
CPC .. A61M 5/142; A61M 5/145; A61M 5/14586; A61M 5/14593; A61M 5/148; A61M 5/152; A61M 5/168; A61M 5/16804; A61M 5/16813; A61M 5/16877; F16K 47/06; F16K 47/12

See application file for complete search history.

(56) References Cited

U.S. PATENT DOCUMENTS

| | | | |
|---|---|---|---|
| 4,634,434 A | 1/1987 | Marino, Jr. et al. | |
| 4,953,594 A | 9/1990 | Von Berg | |
| 8,869,826 B2 | 10/2014 | Chappel et al. | |
| 2005/0224737 A1 | 10/2005 | Mihaylov et al. | |
| 2007/0131296 A1 | 6/2007 | Schinazi et al. | |
| 2007/0255199 A1 | 11/2007 | Dewey | |
| 2012/0191059 A1 | 7/2012 | Cummings et al. | |
| 2017/0241583 A1* | 8/2017 | Schinazi | A61M 5/168 |
| 2018/0008768 A1 | 1/2018 | Prescher et al. | |
| 2018/0280610 A1 | 10/2018 | Stettner | |

FOREIGN PATENT DOCUMENTS

| | | |
|---|---|---|
| DE | 2745317 A1 | 4/1978 |
| DE | 102016212579 | 5/2017 |
| EP | 1486221 A1 | 12/2004 |
| EP | 3381489 A1 | 10/2018 |
| GB | 1600480 A | 10/1981 |
| JP | S63164961 A | 7/1988 |
| JP | 2012527587 A | 11/2012 |
| WO | 2017106408 A1 | 6/2017 |

OTHER PUBLICATIONS

Search Report received in German Application No. 10 2019 200 399.0 dated Nov. 6, 2019, with translation, 14 pages.
Search Report received in International Application No. PCT/EP2020/050218 dated May 11, 2020, with translation, 6 pages.
Written Opinion received in International Application No. PCT/EP2020/050218 dated May 11, 2020, with translation, 5 pages.
Notice of Allowance received in Japanese Application No. 2021-534352 dated May 7, 2024, with translation, 2 pages.

* cited by examiner

MEDICAL PUMP DEVICE FOR CONVEYING A MEDICAL FLUID

CROSS-REFERENCE TO RELATED APPLICATION(S)

This application is the United States national phase entry of International Application No. PCT/EP2020/050218, filed Jan. 7, 2020, and claims the benefit of priority of German Application No. 10 2019 200 399.0, filed Jan. 15, 2019. The contents of International Application No. PCT/EP2020/050218 and German Application No. 10 2019 200 399.0 are incorporated by reference herein in their entireties.

FIELD

The invention relates to a medical pump device for conveying a medical fluid, having an elastomeric membrane, which forms a pump volume for receiving and delivering the medical fluid, wherein the elastomeric membrane is elastically expanded in a filling state of the pump volume at least partially filled with the medical fluid, and wherein, by means of the elastically expanded membrane, a delivery pressure is exerted on the pump volume in order to deliver the medical fluid into a medical fluid-line system connectable in a fluid-conducting manner to the pump volume, and having a throttle device with at least one channel, wherein the channel has an inlet, which is connected in a fluid-conducting manner to the pump volume, and an outlet, which is connectable in a fluid-conducting manner to the medical fluid-line system, and wherein the at least one channel is designed in such a way that the delivery of the medical fluid through the outlet can be finely adjusted to a defined flow rate at the time of manufacture.

BACKGROUND

A medical pump device of this kind is generally known in the field of medicine and is provided for use in infusion therapy. A pump device of this kind can also be designated as an elastomeric infusion pump or medical elastomeric pump. The known pump device has an elastomeric membrane which forms a pump volume for receiving and delivering a medical fluid. During filling of the pump volume with the medical fluid, the membrane is elastically expanded like a balloon. The membrane expanded in this way exerts a delivery pressure on the pump volume. By means of the delivery pressure, the medical fluid can be conveyed into a medical fluid-line system, in the form of a catheter line, connectable in a fluid-conducting manner to the pump device, and can be administered to a patient. In particular to avoid overdosing of the medical fluid, it is necessary here that the medical fluid is delivered at a specific flow rate. In order to ensure this, the known pump device is provided with a throttle device which is intended to throttle the delivery to a defined flow rate. For this purpose, the throttle device has a channel with an inlet and an outlet. The inlet is connected in a fluid-conducting manner to the pump volume. The outlet is connectable in a fluid-conducting manner to the catheter line. In the known pump device, the channel is designed in the form of a hose with a comparatively small effective diameter and thus acts as a flow resistance. The components of the pump device that generate the delivery pressure and/or that conduct fluid are necessarily subject to tolerances. This is associated with a tolerance-affected delivery pressure and thus with a tolerance-affected flow rate. In order to compensate for these tolerances, the channel of the known pump device is designed in such a way that the delivery of the medical fluid through the outlet can be finely adjusted to the defined flow rate at the time of manufacture. In the known pump device, the channel is for this purpose machined with removal of material.

SUMMARY

The object of the invention is to make available a pump device which is of the kind mentioned at the outset and which, compared to the prior art, has improved properties and in particular permits improved fine adjustment of the flow rate at the time of manufacture.

This object is achieved by the fact that the throttle device has at least a first body and a second body, wherein the at least one channel is formed between oppositely arranged surfaces of the two bodies, and wherein the surfaces are movable relative to each other for the fine adjustment of the flow rate at the time of manufacture, in such a way that an effective length of the channel is variable. By means of the solution according to the invention, it is possible in particular to dispense with a material-removing machining of the channel for the fine adjustment of the flow rate at the time of manufacture. Particles of material arise during such material-removing machining. These particles may contaminate the pump device, enter the medical fluid-line system during use of the pump device and ultimately pose a risk to the patient's health, and they therefore have to be carefully removed after the flow rate has been finely adjusted. By virtue of the solution according to the invention, it is not necessary to do this. Instead, the solution according to the invention permits a simple change of the effective length, and thus of the flow resistance, of the channel by means of a relative movement of the oppositely arranged surfaces at the time of manufacture. The resulting change in the length of the channel is reversible, in contrast in particular to a material-removing machining process. That is to say, after the effective length has been shortened, the effective length can if necessary be increased again, and vice versa. Waste material arising during manufacture can thus be avoided. Within the meaning of the invention, fine adjustment at the time of manufacture signifies that, for the purpose of tolerance compensation in a separate method step during or after the production of the pump device, the flow rate is individually adjusted to a defined value. By contrast, in a later state of the pump device when ready for use, the flow rate is preferably not adjustable. For the fine adjustment of the flow rate, the surfaces arranged opposite each other can be movable relative to each other in a linear, pivoting and/or rotating movement. The same applies to the first body and the second body. A first of the surfaces is assigned to the first body. A second of the surfaces is assigned to the second body. The channel is bordered in the circumferential direction partially by the first surface and partially by the second surface. The effective length of the channel runs along an axial direction of the channel between the inlet and the outlet. The effective length can also be designated as the hydraulically effective length and is the length of the channel along which the medical fluid is delivered. The channel can extend in any desired form, in particular in a straight line, flat or spatially curved, helically or spirally.

In one embodiment of the invention, the first body has a cylinder bore, and the second body is designed in the form of a cylinder, wherein the cylinder is fitted into the cylinder bore, and wherein the channel is designed in the form of an at least single-flight helix in a radial direction between the cylinder bore and the cylinder. The helix can also be designated as a screw or a cylindrical spiral. Accordingly, in this embodiment of the invention, the channel winds, preferably with a constant pitch, around the cylinder and/or the cylinder bore. This is a particularly advantageous embodiment of the invention in the sense that a comparatively long effective length of the channel can be achieved with a compact installation space. In relation to a rectilinear channel for example, this permits a comparatively greater diameter of the channel for the same throttle action. In this way, it is possible to avoid fluid-dynamic interface phenomena that may occur in particular in channels with a very small diameter. Such undesired interface phenomena can in particular lead to a delayed onset of the delivery of the medical fluid and/or to a premature blockage of the delivery, even before a desired flow rate has been reached. This situation can be counteracted by this embodiment of the invention. The cylinder bore is preferably a circular cylinder bore. The cylinder is preferably a circular cylinder. The helix preferably has one helical flight at least and in this sense can also have two, three or four helical flights or even a greater number of helical flights than this. Accordingly, the helix has at least one helical flight. However, the helix can also have two, three, four or any number of helical flights. For the fine adjustment of the flow rate, the cylinder and the cylinder bore are movable relative to each other axially and/or in the circumferential direction. The channel is preferably bordered in the circumferential direction partially by an inner lateral face of the cylinder bore and partially by an outer lateral face of the cylinder. In this embodiment of the invention, the surfaces arranged opposite each other are accordingly an inner lateral face of the cylinder bore and an outer lateral face of the cylinder.

In a further embodiment of the invention, the channel is designed in the form of an at least double-flight helix with at least a first helical flight and a second helical flight. In this embodiment of the invention, the shape of the channel can accordingly also be designated as a double helix, double-threaded screw or double-threaded cylindrical spiral. The first helical flight has a first winding direction. The second helical flight has a second winding direction. The first winding direction and the second winding direction can be opposite to each other or in the same sense. The first helical flight has a first pitch. The second helical flight has a second pitch. The first pitch and the second pitch can be dimensioned identically or differently. If the first helical flight and the second helical flight have the same winding directions and the same pitches, the first helical flight and the second helical flight do not form points of intersection and in this sense are separated from each other. Otherwise, particularly in the case of opposite winding directions, the helical flights form points of intersection and in this sense are connected to each other. This embodiment of the invention permits in particular an improved adaptability of the fluidic properties of the channel against the background of the fine adjustment that is to be achieved.

In a further embodiment of the invention, the helical flights have mutually opposite winding directions. For example, the first helical flight can be left-handed and the second helical flight can be right-handed, or vice versa. The helical flights form points of intersection here. This is particularly advantageous in terms of a possible blockage of the channel. In the event of such a blockage of the channel, which can be caused for example by a foreign body or the like, the medical fluid can be conveyed past the blockage by means of the points of intersection. This has the result that the throttling action of the channel is influenced only to a relatively small extent by such a blockage.

In a further embodiment of the invention, the channel is designed by means of a helical profiling, which is arranged on an inner lateral face of the cylinder bore and/or on an outer lateral face of the cylinder. The profiling can be designed in the form of a profile depression and/or a profile elevation. For example, the profiling can be designed in the form of a profile groove introduced into the inner lateral face and/or the outer lateral face. The profiling can be designed by material removal or shaping using a method known in principle in the field of production engineering. For example, the profiling can be designed by means of embossing, etching, grinding or the like. The profiling can have any desired cross-sectional shape. The profiling is preferably at least partially open in the circumferential direction of the channel.

In a further embodiment of the invention, the profiling is produced by means of embossing. Methods suitable for this purpose are known in principle in the field of screw production for example. By means of this embodiment of the invention, it is possible to adhere in particular to narrow dimensional tolerances in the design of the channel. This is particularly advantageous as regards the fine adjustment of the flow rate.

In a further embodiment of the invention, the profiling has a cross-sectional shape that is chosen from a group of cross-sectional shapes consisting of a rectangle, triangle, circle segment, parabola and trapezoid. The aforementioned cross-sectional shapes have proven advantageous as regards the flow characteristics of the channel.

In a further embodiment of the invention, the cylinder and the cylinder bore are joined together with radially elastic pretensioning in such a way that a fluid-tight interference fit is obtained. The fluid-tight interference fit between the cylinder and the cylinder bore counteracts unwanted leakage and ensures that the medical fluid can be delivered in a functionally correct manner along the channel. In this embodiment, it has proven advantageous if the cylinder is made from a dimensionally stable material and the cylinder bore is made from a flexible material, or vice versa. This odd pairing of materials allows the elastic pretensioning to be obtained in a particularly simple way.

In a further embodiment of the invention, the cylinder is made from a dimensionally stable material, and the first body has a flexible hose portion that has the cylinder bore. Metal, glass or a plastic with corresponding material properties can be chosen in particular as the dimensionally stable material. The flexible hose portion is preferably made from a resilient plastic. It has been found that it is thereby possible to achieve a particularly advantageous fluid-tight interference fit between the cylinder and the cylinder bore.

BRIEF DESCRIPTION OF THE DRAWING FIGURES

Further advantages and features of the invention will become clear from the following description of preferred exemplary embodiments of the invention, which are explained with reference to the drawings.

DETAILED DESCRIPTION

Figure 1:
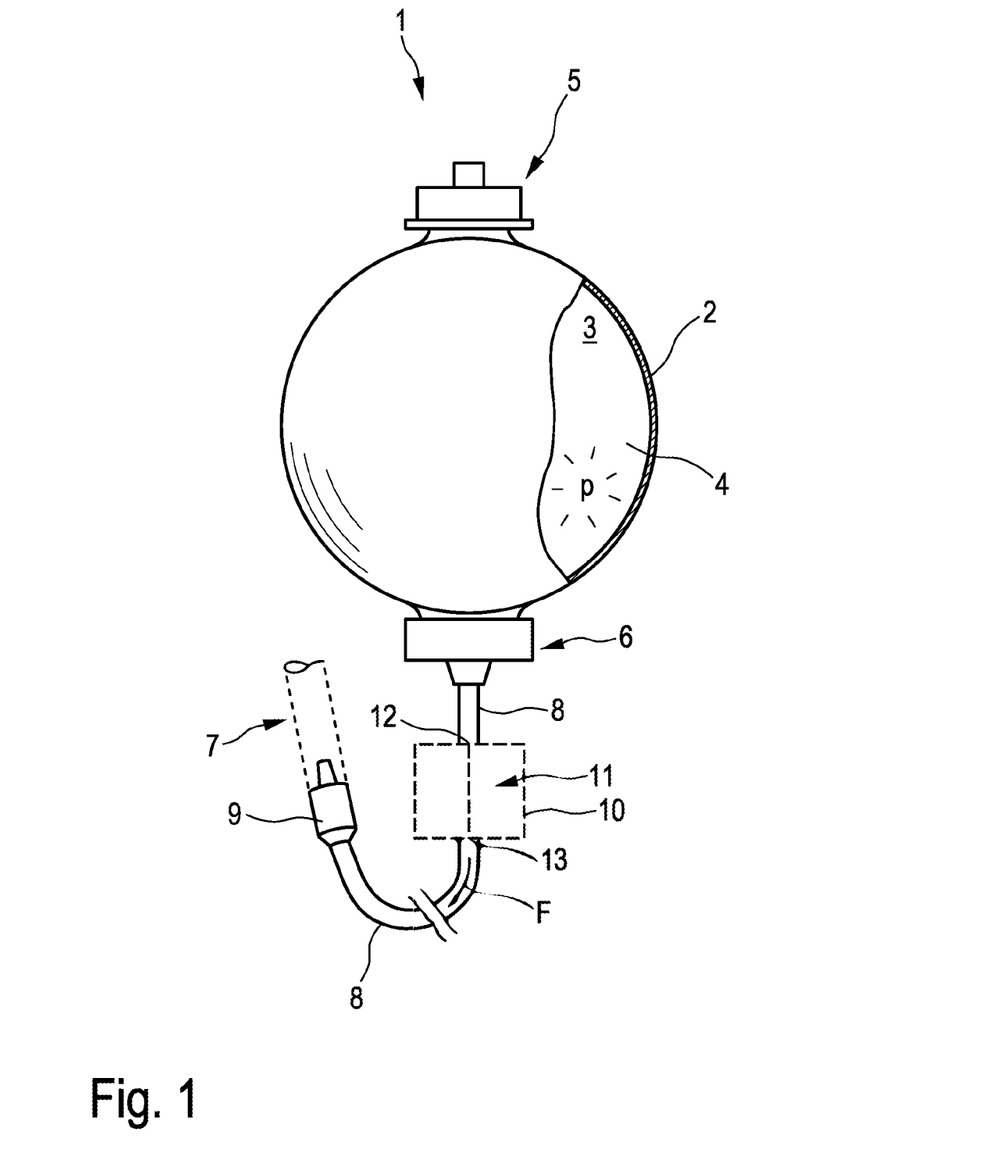
FIG. 1 shows, in a greatly simplified schematic view, an embodiment of a medical pump device according to the invention, which is provided for use in infusion therapy and has a throttle device.

According to FIG. 1, a medical pump device 1 is provided for delivering a medical fluid 4 in the context of outpatient and/or inpatient infusion therapy. The medical pump device 1 can also be designated as an elastomeric infusion pump or a medical elastomeric pump.

The medical pump device 1 has an elastomeric membrane 2 which forms a pump volume 3 for receiving and delivering the medical fluid 4. In the present case, the medical fluid is a liquid medicament not defined in any more detail. With reference to FIG. 1, the medical pump device 1 is shown in a filling state. In this filling state, the elastomeric membrane 2 is flexibly expanded like a balloon on account of a mechanical action of the medical fluid 4. In FIG. 1, the elastomeric membrane 2 is illustrated with an exaggerated wall thickness for graphic reasons. By contrast, in a state when not filled with the medical fluid 4, the membrane 2 is slack or at any rate less elastically expanded. For filling the pump volume 3 or the membrane 2 with medical fluid 4, a reclosable filling nozzle 5 is provided, which is attached to the membrane 2 in a fluid-tight manner known in principle.

The elastically expanded elastomeric membrane 2 subjects the pump volume 3 to a delivery pressure p. By means of the delivery pressure p produced in this way, the medical fluid 4 can be delivered through a passage nozzle 6, connected in a way known in principle and in a fluid-conducting manner to the elastomeric membrane 2, from the pump volume 3 into a medical fluid-line system 7 that is connected in a fluid-conducting manner to the pump device 1. In FIG. 1, the medical fluid-line system 7 is only shown in a greatly simplified schematic and partially cut-away dashed-line view. In the present case, the medical fluid-line system is a patient line 7 of a well known central venous catheter, through which the medical fluid 4 can be administered to a patient (not shown in any detail in the drawing). In the present case, starting from the passage nozzle 6, the pump device 1 is connectable in a fluid-conducting manner to the patient line 7 by means of a hose line 8. For this purpose, the hose line 8, at its end directed toward the pump volume 3, is connected non-releasably in the present case to the passage nozzle 6. At its opposite end, the hose line 8 has a fluid connector 9. In the present case, the fluid connector is designed in the form of a well known Luer attachment 9. The Luer attachment 9 is provided for connection to a complementary Luer attachment of the patient line 7. In an embodiment not shown in the drawing, the fluid connector 9 can be designed in the form of an attachment marketed under the federally registered trademark NIRFit®.

In the present case, the medical pump device 1 is dimensioned in such a way that it can be readily worn on the body by a patient and can be used without an external energy supply, particularly in the context of outpatient therapy. The medical pump device 1 is accordingly light and dimensionally compact, wherein in the present case the pump volume 3 has a nominal size of 400 ml. It goes without saying that the pump volume 3 may also differ from this, for example dimensioned with a nominal size of between 50 ml and 750 ml.

Figure 2:
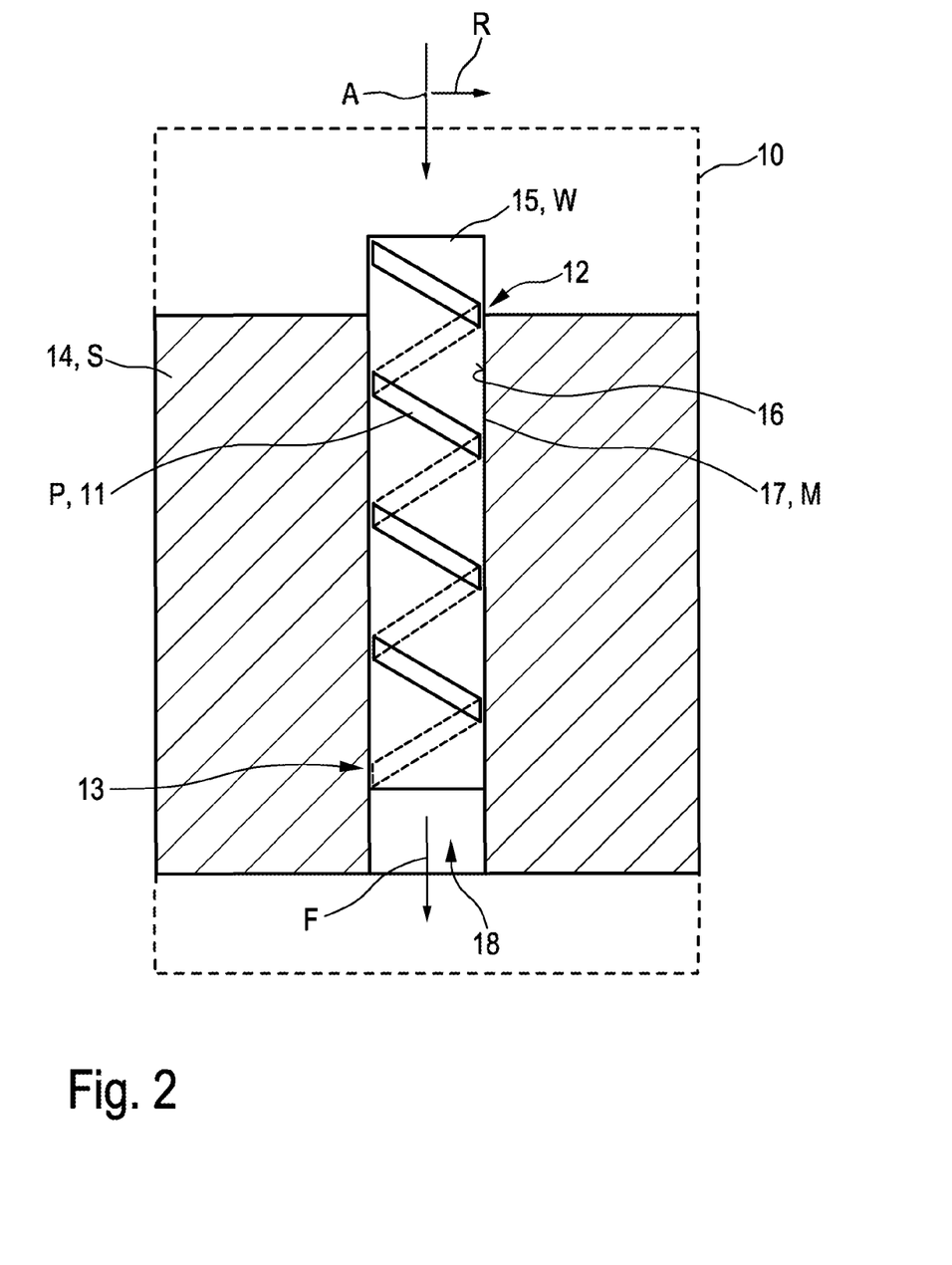
FIG. 2 shows, in a greatly simplified schematic and partially sectioned detail view, the throttle device of the pump device according to FIG. 1, wherein the throttle device has in particular a second body in the form of a cylinder.

In particular to rule out overdosing of the medical fluid 4, a suitable throttling of the delivery pressure p is necessary. For this purpose, the medical pump device 1 moreover has a throttle device 10. The throttle device 10 is in the present case arranged outside the pump volume 3 in the region of the hose line 8, but this does not necessarily have to be the case. In an embodiment not shown in detail in the drawing, the throttle device 10 can be integrated for example in the pump volume 3 or the passage nozzle 6. The throttle device 10 has a channel 11, which is shown in a greatly simplified schematic view in FIG. 1. The channel has an inlet 12 and an outlet 13. The inlet 12 is in the present case connected in a fluid-conducting manner to the pump volume 3 via the hose line 8 and the passage nozzle 6. The outlet 13 is in the present case connected in a fluid-conducting manner to the patient line 7 via the hose line 8 and the fluid connector 9.

In particular, the elastomeric membrane 2 is subject to dimensional tolerances arising from its manufacture. The properties of the material of the elastomeric membrane 2 may also be subject to certain tolerances. These tolerances produce a tolerance-affected delivery pressure p and thus a tolerance-affected delivery of the medical fluid 4. This is undesirable from the medical point of view, since a flow rate F of the medical fluid 4 that can be administered with the medical pump device 1 has to be achieved as exactly as possible. To ensure that this is the case, the channel 11 is designed in such a way that the delivery of the medical fluid 4 through the outlet 13 can be finely adjusted to a defined flow rate F at the time of manufacture. Accordingly, by way of the fine adjustment by means of the channel 11 at the time of manufacture, in particular dimensional or material tolerances of the elastomeric membrane 2 can be compensated. Further structural and functional features of the throttle device 10 can be seen in particular from FIG. 2.

The throttle device 10 has a first body 14 and a second body 15. The channel 11 is formed between oppositely arranged surfaces 16, 17 of the two bodies 14, 15. A first surface 16 is assigned to the first body 14. A second surface 17 is assigned to the second body 15. To finely adjust the flow rate F and thus effect the above-described tolerance compensation, the two surfaces 16, 17 are movable relative to each other in such a way that an effective length of the channel 11 is variable. The effective length (not defined in any more detail) of the channel 11 runs between the inlet 12 and the outlet 13. The smaller the effective length of the channel 11, the lesser a flow resistance and thus a throttling action on the delivery of the medical fluid 4. The greater the effective length of the channel 11, the greater the flow resistance and thus a throttling action on the delivery of the medical fluid 4. Accordingly, a reduction in the effective length can produce an increase in the flow rate F and, conversely, an increase in the effective length can produce a reduction in the flow rate F for the purpose of the fine adjustment. For the fine adjustment of the flow rate F, the second body 15 is in the present case moved in an axial direction A relative to the first body 14. As can be seen from FIG. 2, this changes the effective length of the channel 11, formed between the surfaces 16, 17, and thus changes the flow resistance of the channel 11. If, starting from the configuration that can be seen in FIG. 2, the second body 15 is moved farther downward in the axial direction A, with respect to the drawing plane of FIG. 2, this produces an increase in the effective length of the channel 11. If the second body 15 is moved upward in the opposite direction for this purpose, this produces a reduction in the effective length of the channel 11. In the present case, provision is made that the above-described adaptation of the effective length, i.e. the fine adjustment, takes place at the time of manufacture and thus in a separate production and/or assembly step. By contrast, an adaptation of the effective length of the channel 11 in a state when the pump device 1 is ready for use is not provided for in the present case.

In the present case, the first body 14 has a cylinder bore 18, and the second body is designed in the form of a cylinder 15 and fitted into the cylinder bore 18. The channel is designed in the form of an at least single-flight helix 11 in a radial direction R between the cylinder bore 18 and the cylinder 15. The helix 11 can also be designated as a screw or cylindrical spiral. By virtue of this design of the channel 11, a long effective length of the channel 11 can be achieved with a comparatively compact structural volume. Compared to a channel extending for example in a straight line in axial direction A between the inlet 12 and the outlet 13, a comparatively greater effective cross section can be achieved with the same flow resistance and thus with the same throttling action. In this way, it is possible to counteract interface phenomena that may be associated with a very small effective diameter. In particular, by virtue of the design of the channel in the form of the helix 11, it is possible to avoid a delayed onset of the delivery and/or a premature blockage of the delivery on account of said interface phenomena.

The cylinder bore 18 is designed as a circular cylinder in the present case. Accordingly, the cylinder 15 is a circular cylinder. The helix 11 extends coiling in the circumferential direction with a pitch (not defined in any more detail) relative to the axial direction A over the entire length of the cylinder 15. The helix 11 has a constant pitch in the present case.

Figure 5:
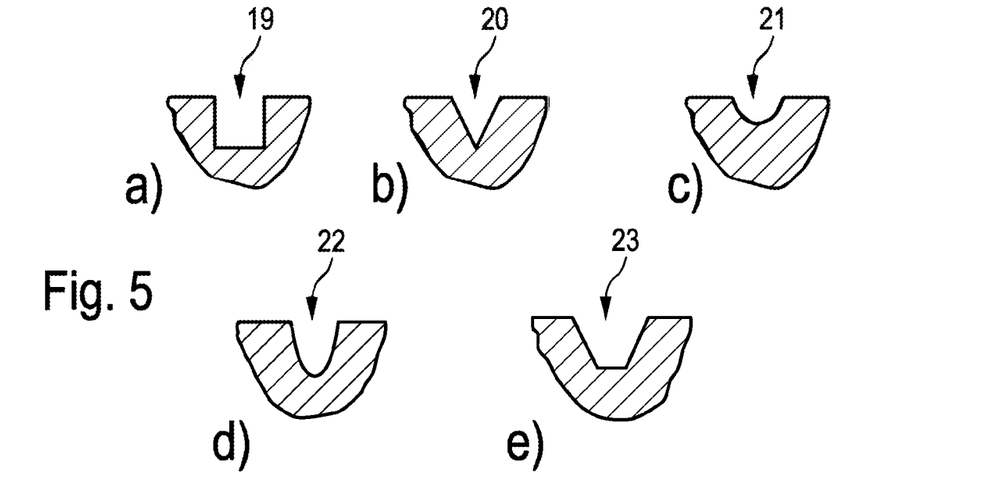
FIG. 5 shows different cross-sectional shapes of a channel of the throttle device according to FIGS. 1 and 2, in each case in a greatly simplified and cut-away schematic cross-sectional view.

The channel 11 is designed here by means of a helical profiling P, which in the present case is arranged on an outer lateral face M of the cylinder 15. The profiling P has a rectangular cross-sectional shape (FIG. 5a) and is produced by means of embossing. For this purpose, the cylinder 15 is produced from a dimensionally stable material W which can be embossed by means of a method that is well known in the field of production engineering.

Departing from the cross-sectional shape in the form of a rectangle 19 as can be seen in FIG. 5a), further cross-sectional shapes are alternatively possible and are shown in the further figures FIGS. 5b) to 5e). Thus, the profiling P can alternatively have a cross-sectional shape in the form of a triangle 20, a circle segment 21, a parabola 22 or a trapezoid 23.

The first body 14 has a flexible hose portion S through which the cylinder bore 18 extends. The cylinder bore 18 is designed to be flexibly resilient at least in the radial direction R. The cylinder 15 is pressed into the cylinder bore 18 under radially elastic pretensioning of the latter, such that a fluid-tight interference fit between the cylinder 15 and the cylinder bore 18 is obtained. This ensures that the medical fluid 4 is delivered in a functionally correct manner along the channel 11 and is not for example forced past the outer circumference of the cylinder 15.

Figure 3:
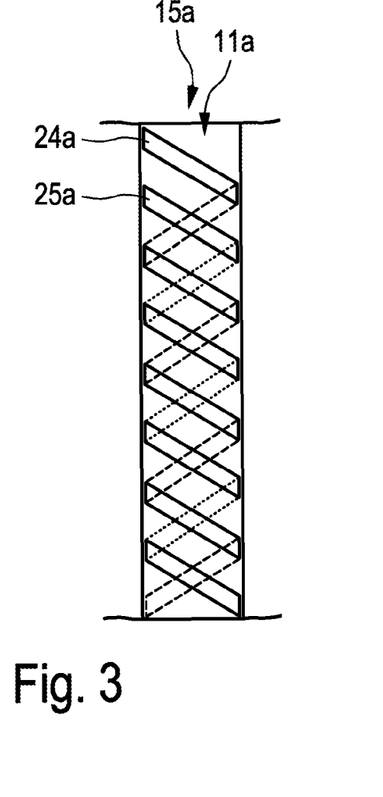
FIG. 3 shows, in a greatly simplified schematic detail view, a further embodiment of a cylinder for a throttle device according to FIGS. 1 and 2.

FIG. 3 shows a further embodiment of a cylinder 15a which can be fitted instead of the cylinder 15 into the cylinder bore 18. The cylinder 15a substantially corresponds to the cylinder 15 in terms of its design features and functional features. To avoid repetition, reference is made to the disclosure in connection with the cylinder 15, which disclosure correspondingly applies for the cylinder 15a. Only the differences between the cylinder 15a and the cylinder 15 are discussed below. In contrast to the cylinder 15, a channel 11a is provided. The channel is designed in the form of a double-flight helix 11a and has a first helical flight 24a and a second helical flight 25a. The first helical flight 24a has a first winding direction (not described in more detail). The second helical flight 25a has a second winding direction (not described in more detail). The two winding directions correspond. In addition, the helical flights 24a, 25a have an identical pitch. By means of the double-flight configuration of the helix 11a, it is possible in particular to counteract an undesired blockage of the channel 11a. For example, if the helical flight 24a is clogged by a foreign body, the medical fluid can still be delivered along the further helical flight 25a, and vice versa.

Figure 4:
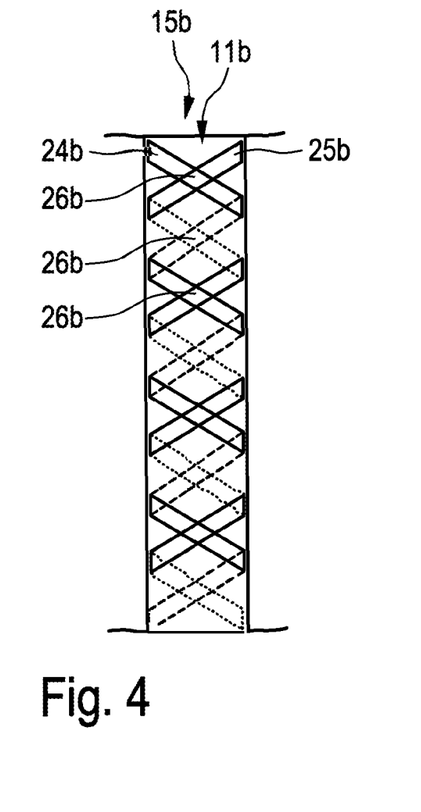
FIG. 4 shows, in a greatly simplified schematic detail view, a further embodiment of a cylinder for a throttle device according to FIGS. 1 and 2.

FIG. 4 shows a further embodiment of a cylinder 15b. To avoid repetition, reference is again made to the disclosure in connection with the cylinder 15 and the cylinder 15a, each of which disclosures applies correspondingly for the cylinder 15b. Only the differences between the cylinder 15b and the cylinder 15a are discussed below. The cylinder 15b has in turn a channel in the form of a double-flight helix 11b which is designed with a first helical flight 24b and a second helical flight 25b. The helical flights 24b, 25ba have winding directions opposite to each other (not described in more detail). In this way, the helical flights 24b, 25b form points of intersection 26b. The helical flights 24b are thus connected to each other in a fluid-conducting manner.

Figure 6:
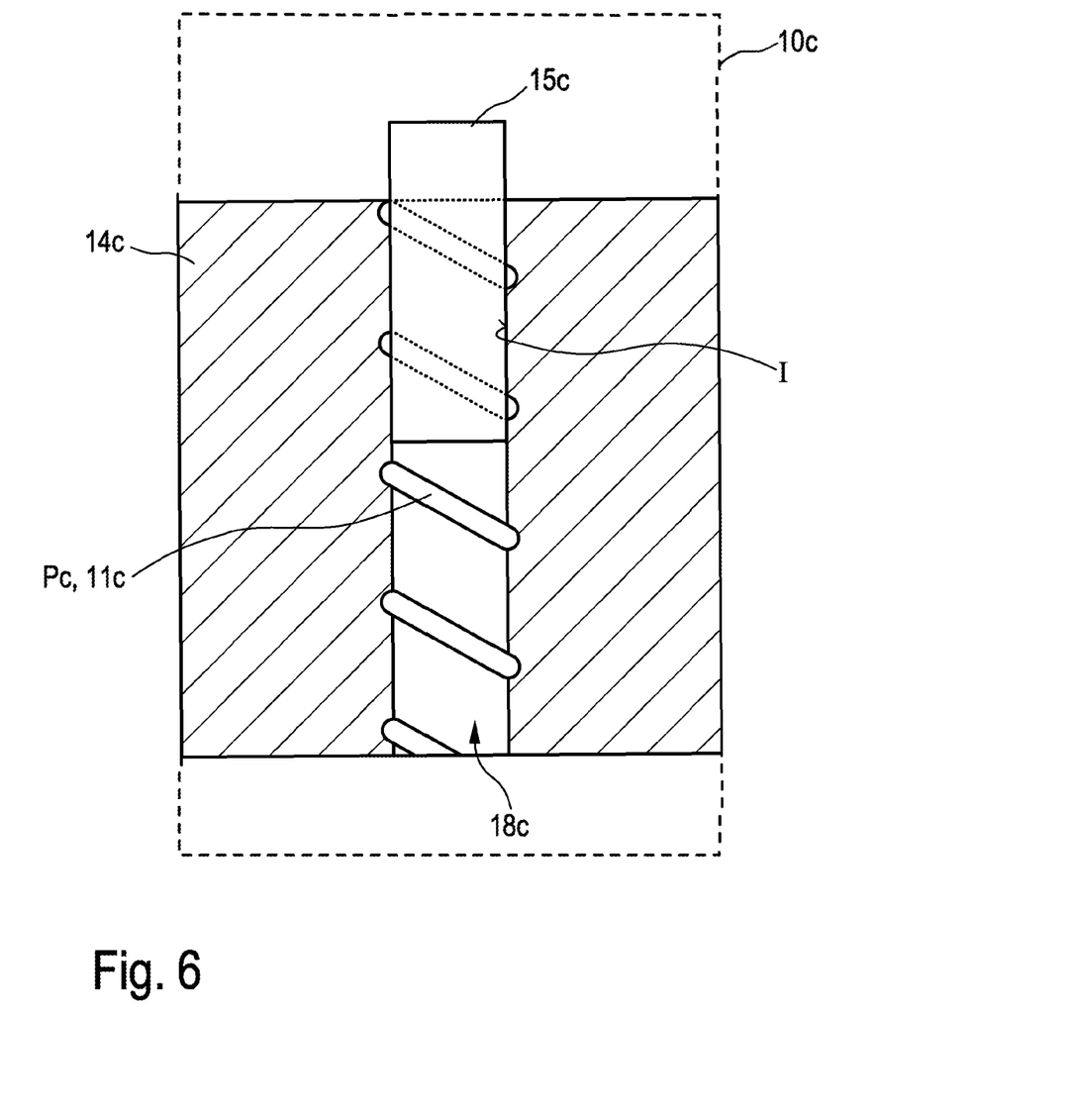
FIG. 6 shows, in a view according to FIG. 2, a further embodiment of a throttle device for the pump device according to FIG. 1.

FIG. 6 shows a throttle device 10c in a greatly simplified schematic view. The throttle device 10c can be used instead of the throttle device 10 for the medical pump device 1 according to FIG. 1. In terms of its design and function, the throttle device 10c largely corresponds to the throttle device 10. To avoid repetition, reference is therefore made to the disclosure in connection with the throttle device 10, which disclosure applies correspondingly to the throttle device 10c. The throttle device 10c has a channel 11c. The channel is in turn designed in the form of a single-flight helix 11c between a cylinder bore 18c and a cylinder 15c. The cylinder 15c is shown shortened in the axial direction for graphic reasons, in order to better reveal the helix 11c. In contrast to the channel 11, the channel 11c is formed by means of a profiling Pc which is arranged on an inner lateral face I of the cylinder bore 18c. Accordingly, the profiling Pc is embossed into the inner lateral face I. The profiling Pc in the present case has a cross-sectional shape in the form of a circle segment 21 according to FIG. 5c), but this does not necessarily have to be the case. Instead of the circle segment 21, the further cross-sectional shapes according to FIG. 5 or other kinds of cross-sectional shapes can also be provided.

The invention claimed is:

1.

A medical pump device for conveying a medical fluid, the medical pump device comprising:
an elastomeric membrane, which forms a pump volume for receiving and delivering the medical fluid,
wherein the elastomeric membrane is elastically expanded in a filling state of the pump volume at least partially filled with the medical fluid,
and wherein, the elastically expanded elastomeric membrane exerts a delivery pressure on the pump volume in order to deliver the medical fluid into a medical fluid-line system connectable in a fluid-conducting manner to the pump volume, the medical pump device further comprising a throttle device with a channel, wherein the channel has an inlet, which is connected in a fluid-conducting manner to the pump volume, and an outlet, which is connectable in a fluid-conducting manner to the medical fluid-line system, and wherein the channel is designed in such a way that a delivery of the medical fluid through the outlet is adjustable to a defined flow rate, wherein the throttle device has at least a first body and a second body, wherein the channel is formed between oppositely arranged surfaces of the first body and the second body, and wherein the surfaces are movable relative to each other for finely adjusting the defined flow rate in such a way that an effective length of the channel is variable, and wherein the first body has a cylinder bore, and the second body comprises a cylinder, wherein the cylinder is fitted into the cylinder bore, and wherein the channel comprises an at least single-flight helix in a radial direction between the cylinder bore and the cylinder.

2. The medical pump device according to claim 1, wherein the at least single-flight helix comprises an at least double-flight helix with at least a first helical flight and a second helical flight.

3. The medical pump device according to claim 2, wherein the first helical flight and the second helical flight have mutually opposite winding directions.

4. The medical pump device according to claim 1, wherein the channel is designed by a helical profiling, which is arranged on an inner lateral face of the cylinder bore and/or on an outer lateral face of the cylinder.

5. The medical pump device according to claim 4, wherein the helical profiling is produced by embossing.

6. The medical pump device according to claim 4, wherein the helical profiling has a cross-sectional shape that is chosen from a group of cross-sectional shapes consisting of a rectangle, a triangle, a circle segment, a parabola and a trapezoid.

7. The medical pump device according to claim 1, wherein the cylinder and the cylinder bore are joined together with radially elastic pretensioning in such a way that a fluid-tight interference fit is obtained.

8. The medical pump device according to claim 1, wherein the cylinder is made from a dimensionally stable material and the first body has a flexible hose portion that has the cylinder bore.

\* \* \* \* \*